United States Patent [19]

Polichnowski

[11] Patent Number: 4,581,473

[45] Date of Patent: Apr. 8, 1986

[54] PREPARATION OF ETHYLIDENE DIACETATE

[75] Inventor: Stanley W. Polichnowski, Kingsport, Tenn.

[73] Assignee: Eastman Kodak Company, Rochester, N.Y.

[21] Appl. No.: 229,808

[22] Filed: Jan. 30, 1981

[51] Int. Cl.$^4$ .................. C07C 67/00; C07C 69/16
[52] U.S. Cl. .................................. 560/263; 560/265; 560/266; 562/607
[58] Field of Search ..................... 560/263; 562/607

[56] References Cited

U.S. PATENT DOCUMENTS

| 3,579,566 | 5/1971 | Fenton | 560/263 |
| 4,221,918 | 9/1980 | Suzuki | 560/263 |

FOREIGN PATENT DOCUMENTS

| 1538782 | 1/1979 | United Kingdom | 560/232 |

Primary Examiner—Vivian Garner
Attorney, Agent, or Firm—J. Frederick Thomsen; Daniel B. Reece, III

[57] ABSTRACT

Process for the preparation of ethylidene diacetate by hydrogenating acetic anhydride in the presence of a homogeneous rhodium catalyst, methyl iodide and lithium iodide.

2 Claims, No Drawings

PREPARATION OF ETHYLIDENE DIACETATE

This invention relates to a novel process for the preparation of ethylidene diacetate by hydrogenating acetic anhydride.

An economically advantageous process for the preparation of acetic anhydride by the carbonylation of methyl acetate has been reported in the patent literature. See, for example, Belgian Pat. No. 819,455, British Published Patent Application 2,013,184, Japanese Published Patent Applications 75-47921 and 75-47922 and U.S. Pat. Nos. 3,927,078 and 4,046,807. Not only is acetic anhydride itself an important chemical, for example as an acetylating agent in the manufacture of cellulose acetate and other esters, but it can be converted to ethylidene diacetate. The ethylidene diacetate can be converted to vinyl acetate which presently is derived primarily from petroleum.

Very little prior art exists concerning the hydrogenation of acetic anhydride. The hydrogenation of acetic anhydride to ethylidene diacetate and acetic acid with a catalyst consisting of a Group VIII noble metal and a biphyllic ligand selected from the group consisting of trihydrocarbyl phosphines, arsines, and stibines is disclosed in U.S. Pat. No. 3,579,566. With these catalysts the reaction rate was slow. Depending upon the reaction conditions and catalyst used, ethyl acetate and acetic acid were produced, along with the desired ethylidene diacetate product. The co-production of acetic anhydride and ethylidene diacetate by the carbonylation of methyl acetate in the presence of hydrogen, a Group VIII noble metal catalyst and methyl iodide is disclosed in Belgian Pat. No. 839,321. The preparation of ethylidene diacetate from acetic anhydride using a supported palladium catalyst in the presence of a strong acid, i.e., HCl, HF, or methane sulfonic acid, is disclosed in Belgian Pat. No. 879,178. When HCl was the acid used, large amounts of 1-chloroethylacetate were produced along with the desired ethylidene diacetate and acetic acid products.

The process of this invention comprises hydrogenating at elevated pressure and temperature acetic anhydride in the presence of a catalytic amount of a homogeneous rhodium compound, methyl iodide and lithium iodide. The rhodium catalyst is an ionic rhodium species which forms as the result of a rhodium compound such as a rhodium halide or oxide contacting an iodine compound such as lithium iodide, methyl iodide, hydrogen iodide or iodine in the presence of carbon monoxide. By characterizing the catalyst as homogeneous is meant that the catalytic species is soluble in the reaction medium. The catalyst employed initially can be a soluble rhodium carbonyl compound such as $Rh_2(CO)_4Cl_2$ which when contacted with an iodine compound forms the catalyst. The rhodium also can be fed initially as a halide such as $RhCl_3.xH_2O$ or an oxide such as $Rh_2O_3$. When the rhodium is fed as a halide or oxide, the carbon monoxide required for the generation of the catalytically-active rhodium species can be supplied in the gas fed to the hydrogenation reactor or it can be derived, as a decomposition product, from the acetic anhydride present. A carbon monoxide pressure of about 10 psig to 500 psig can be maintained during hydrogenation. It has been found that carbon monoxide pressure can inhibit the reaction or hydrogenation rate when high total reaction pressures are employed.

The concentration of the rhodium can be varied substantially depending on such factors as the temperature and pressure employed, the space-time yield desired, etc. Generally, rhodium concentrations in the range of about 50 to 5000 ppm, based on the total weight of the materials fed to the reactor, will give good results when using appropriate pressures and temperatures. Rhodium concentrations (same basis) of about 500 to 2500 will most often be used. The particular rhodium compound charged to the hydrogenation reactor is not critical so long as it is soluble in the reaction medium or results in the formation of a soluble form of rhodium.

The hydrogenation-effective temperatures and pressures employed in the process of this invention also can be varied substantially. Not only are temperature and pressure interdependent with respect to reaction rate but each also is dependent upon catalyst concentrations. Temperatures in the range of about 100° to 225° C. may be used with the preferred temperatures being from about 150° to 190° C. Pressures (total reaction pressure) in the range of about 100 to 5000 psig may be used, although pressures of about 500 to 3000 psig are preferred.

The amount of methyl iodide employed should be in the range of about 5 to 35, preferably about 10 to 20, weight percent based on the weight of acetic anhydride fed to the hydrogenation reactor. Although the process is operable when no lithium iodide is included in the reaction mixture, its absence results in the formation of undesirably large amounts of acetic acid. For this reason lithium iodide should be present in a concentration of about 0.1 to 5.0, preferably about 0.3 to 3.0, weight percent based on the total weight of acetic anhydride fed to the reactor. The mole ratio of lithium iodide to rhodium normally is in the range of about 4 to 300 with ratios of 5 to 100 being preferred. If desired, acetic acid can be included in the materials fed to the hydrogenation reactor. However, since acetic acid is a co-product of the process, its presence, especially during the continuous operation of the process, in the reactor feed normally is not necessary.

The process of the invention is further illustrated by the following examples.

EXAMPLES 1-11

Acetic anhydride (800 g) was hydrogenated for 2 hours in the presence of rhodium charged as $RhCl_3.xH_2O$ and acetic acid (100 g) using different temperatures and total autoclave pressures and varying amounts of methyl iodide and lithium iodide. The acetic anhydride, acetic acid, rhodium chloride, methyl iodide and lithium iodide (when used) were loaded into a 1.8 L Hastelloy B autoclave fitted with a stirrer. The autoclave was purged with carbon monoxide and then carbon monoxide pressure (Initial CO, psig) was placed on the autoclave. The autoclave was sealed and heated and stirred until reaction temperature was reached, at which time additional hydrogen gas was added to increase the autoclave internal pressure to a predetermined value. The time at which the autoclave internal pressure reached the predetermined value was taken as the start of the 2 hour reaction time. Reactor pressure was maintained at the present value during the experiment by adding hydrogen gas at the same rate at which it was consumed by the reactants. When the predetermined reaction time was completed the autoclave was cooled by a stream of cold air. After the gas was vented from the autoclave the reaction product was analyzed by gas chromatographic methods.

Table I shows the temperature (°C.) and pressure (Initial CO and Total, psig) used, the amounts of RhCl$_3$.xH$_2$O (g) and methyl and lithium iodide (CH$_3$I, LiI, g.) charged, and the amounts (in moles) of acetic acid (HOAc) and ethylidene diacetate (EDA) produced.

TABLE I

| Example | Temp. | Initial CO Pressure | Total Pressure | RhCl$_3$.xH$_2$O | LiI | CH$_3$I | EDA | HoAc |
|---------|-------|---------------------|----------------|------------------|-------|---------|------|------|
| 1 | 175 | 100 | 750 | 0.62 | 3.18 | 100 | 0.26 | — |
| 2 | 175 | 100 | 1500 | 0.62 | 3.18 | 100 | 0.72 | 0.84 |
| 3 | 175 | 100 | 2500 | 0.62 | 3.18 | 100 | 1.12 | 1.22 |
| 4 | 175 | 0 | 1500 | 0.62 | 3.18 | 100 | 0.76 | 0.93 |
| 5 | 175 | 1000 | 2500 | 0.62 | 3.18 | 100 | 0.27 | — |
| 6 | 175 | 100 | 1500 | 0.62 | 25.39 | 100 | 0.66 | 0.80 |
| 7 | 175 | 100 | 1500 | 1.24 | 50.78 | 100 | 1.25 | 1.35 |
| 8 | 175 | 100 | 1500 | 0.62 | 3.18 | 25 | 0.26 | 0.25 |
| 9 | 175 | 100 | 1500 | 0.62 | 3.18 | 50 | 0.41 | 0.45 |
| 10 | 130 | 100 | 2500 | 2.48 | 12.70 | 100 | 0.81 | 0.81 |

The invention has been described in detail with particular reference to preferred embodiments thereof, but it will be understood that variations and modifications can be effected within the spirit and scope of the invention.

I claim:

1. Process for the preparation of ethylidene diacetate which comprises hydrogenating acetic anhydride at about 100° to 225° C. and about 100 to 5000 psig in the presence of a catalytic amount of a homogeneous rhodium catalyst, about 5–35 weight percent methyl iodide, based on the amount of acetic anhydride, and about 0.1 to 5.0 weight percent lithium iodide, based on the weight of acetic anhydride.

2. Process according to claim 1 for the preparation of ethylidene diacetate which comprises hydrogenating acetic anhydride at about 150° to 190° C. and about 500 to 3000 psig in the presence of a catalytic amount of a homogeneous rhodium catalyst, 10 to 20 weight percent of methyl iodide and about 0.3 to 3.0 weight percent lithium iodide, based on the weight of the acetic anhydride.

* * * * *